United States Patent [19]

Bauer et al.

[11] Patent Number: 5,041,111
[45] Date of Patent: Aug. 20, 1991

[54] OPERATING INSERT FOR A RESECTOSCOPE WITH SEALING MEANS

[75] Inventors: Siegfried Bauer, Heidelsheim; Ernst Falk, Sternenfels-Diefenbach, both of Fed. Rep. of Germany

[73] Assignee: Richard Wolf GmbH, Knittlingen, Fed. Rep. of Germany

[21] Appl. No.: 414,973

[22] Filed: Sep. 29, 1989

[30] Foreign Application Priority Data

Oct. 22, 1988 [DE] Fed. Rep. of Germany ....... 3836120

[51] Int. Cl.$^5$ .............................................. A61B 17/36
[52] U.S. Cl. ....................................... 606/47; 604/167
[58] Field of Search ..................................... 606/45–47, 606/41, 49; 604/167; 411/542, 544

[56] References Cited

U.S. PATENT DOCUMENTS

| | | | |
|---|---|---|---|
| 2,102,270 | 12/1937 | Hyams | 606/49 |
| 4,325,374 | 4/1982 | Komiya | 606/47 |
| 4,485,812 | 12/1984 | Harada et al. | 606/47 |
| 4,503,855 | 3/1985 | Maslanka | 606/47 |
| 4,718,419 | 1/1988 | Okada | 606/47 |

Primary Examiner—Max Hindenburg
Attorney, Agent, or Firm—Panitch Schwarze Jacobs & Nadel

[57] ABSTRACT

An operating insert to be passed through a resectoscope shaft comprises a channel for an axially displaceable cutting loop which extends parallel to an optical system through the operating insert. The cutting loop has branches secured within a tube and merging at their proximal ends into an electrode stem which extends beyond the shaft as far as an electrode carrier. An annular cylindrical sealing element of plastics material or the like is secured on the stem or on the inner side of the channel and bears via sealing projections against the inner surface of the cutting loop so as to prevent the passage of fluid to the proximal end of the channel while allowing axial movement of the stem and the tube within the channel.

12 Claims, 2 Drawing Sheets

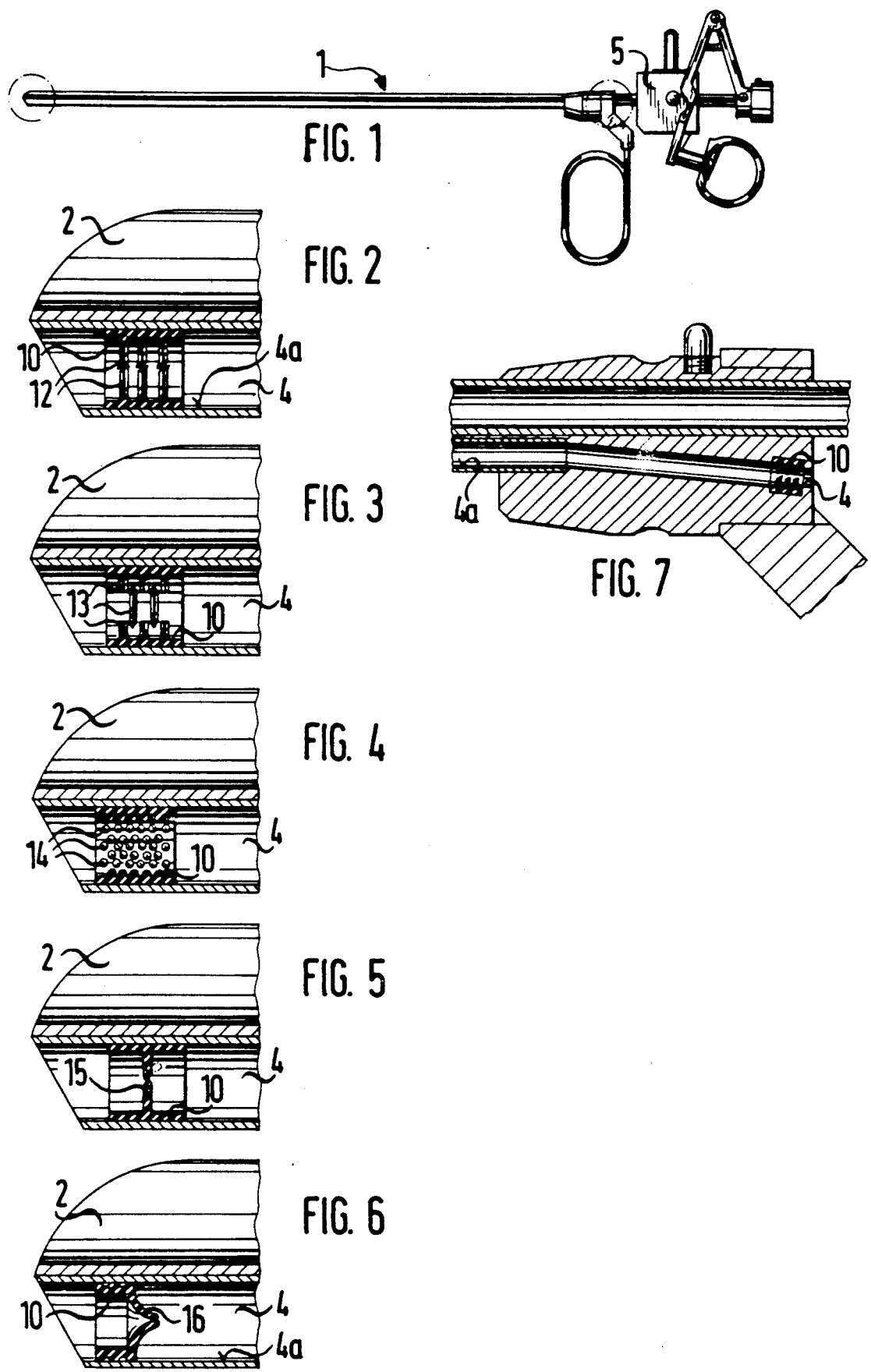

OPERATING INSERT FOR A RESECTOSCOPE WITH SEALING MEANS

BACKGROUND TO THE INVENTION

The invention is based on a resectoscope of the type comprising an operating insert arranged within a shaft and receiving therein an optical system and a channel for an axially displaceable cutting loop. The cutting loop has two proximally extending loop branches which are secured within a thin-walled tube and have proximal ends which merge into an electrode stem which may be releasably secured in an electrode carrier.

Because the proximal end of the cutting loop which is to be supplied with high-frequency current extends partially clear of the operating insert to the electrode carrier, a small quantity of flushing liquid present in the bladder may emerge in an uncontrolled manner at the end of the channel situated in the operating insert and receiving the stem of the cutting loop. Consequently the surgeon, whose face is positioned in direct proximity to the liquid outlet point during observation of the resection, is exposed to a risk of infection.

SUMMARY OF THE INVENTION

It is accordingly an object of the invention to prevent the emergence of flushing liquid at the proximal end of the channel receiving the stem of the cutting loop in the case of resectoscopes of the aforementioned type.

This object is achieved in accordance with the invention, in that a sealing element, preferably a plastics material element of cylindrical form, is fastened to the stem or on the inner side of the channel, and has sealing projections which bear against the inner side of the channel or against the outer periphery of the tube or the stem of the operating insert in a sealing manner. Preferably, the distal end of the sealing element engages with the tube which secures the loop branches, and has a cylindrical constriction provided with sealing projections such as lips or pins which bear in a sealing manner against the inner surface of the channel receiving the stem of the cutting loop, without increasing the frictional resistance to axial displacement of the cutting loop.

Alternatively, the cylindrical sealing ring of plastics material is fastened to the inner surface of the channel and has at least one inwardly directed lip or radially inwardly directed pins for sealing contact with the tube or the stem of the cutting electrode.

BRIEF DESCRIPTION OF THE DRAWINGS

Further objects and advantages of the invention will become apparent from the following detailed description when read with reference to the accompanying drawings which illustrate preferred embodiments of the invention.

In the drawings:

FIG. 1 shows a schematic view of an operating insert showing the position of the sealing element;

FIGS. 2 to 6 show the views of the operating insert with various embodiments of the sealing element;

FIG. 7 shows the coupling cone of the operating insert with the sealing element of the first embodiment shown in FIG. 2;

DETAILED DESCRIPTION OF THE PREFERRED EMBODIMENTS

Figure 8:
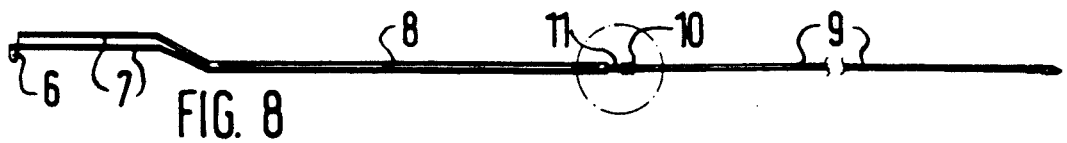
FIG. 8 shows a cutting loop, incorporating a sealing element.
Figure 9:
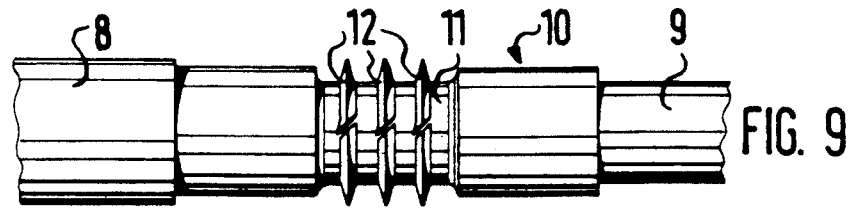
FIGS. 9 to 13 show partial views of the cutting loop according to FIG. 8, illustrating different sealing elements.

The resectoscope comprises a shaft which is not illustrated, an operating insert 1 into which an optical system 2 may be releasably inserted and a channel 4 for receiving a cutting loop or rather its proximal stem. The operating insert is provided at its proximal end with an axially displaceable electrode carrier 5. The cutting loop 6 to 10 comprises the loop member 6, of which the two branches 7 extend through a tube 8 and are secured in the tube 8. These branches 7 merge at the proximal end of the tube 8 into a stem 9 which is connected to the carrier 5 and may be connected to a high-frequency generator via a connecting lead.

As shown in FIGS. 2 to 6, a sealing element 10 formed from an appropriate plastics material is provided, said element being of cylindrical form and engaging in a fixed manner at its distal end with the tube 8. As shown in FIGS. 9 to 12, this sealing element 10 is provided with a cylindrical constriction 11. In the embodiment shown in FIG. 9 the constriction 11 is provided with transversely slotted encircling sealing lips 12 which project beyond the circumference of the tube 8 and bear in a sealing manner against the inner surface of the channel 4.

Figure 10:
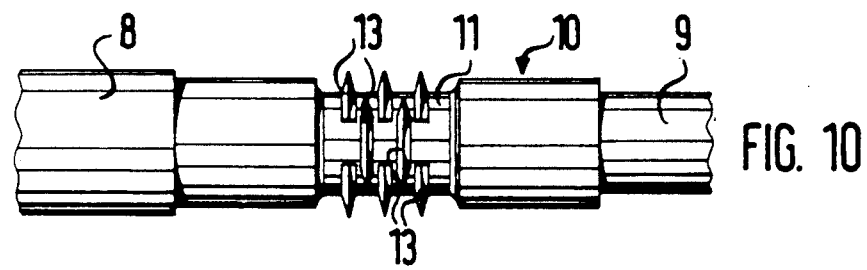

In an alternative embodiment shown in FIG. 10, the lips 13 are part-circular and arranged in a staggered manner such that their ends lie close to one another and overlap each other.

Figure 11:
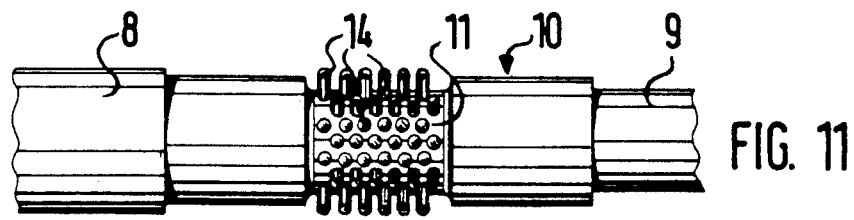

Alternatively, in FIG. 11, the constriction 11 is provided with projections 14 in the form of pins extending radially beyond the circumference of the tube 8, which lie close to each other and are placed in mutual contact by deformation when the cutting loop is inserted into the channel 4.

Figure 12:
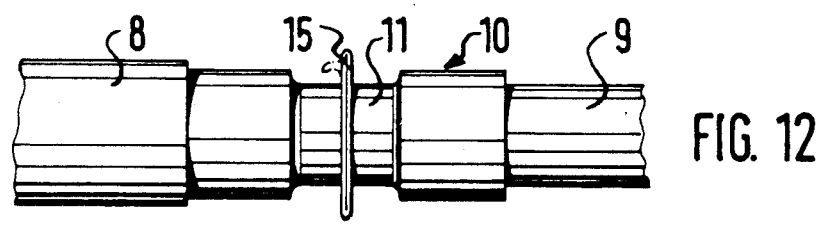

Alternatively, in FIG. 12, the constriction 11 is provided with one annular lip 15 only, which forms the seal in the channel 4 of the operating insert.

Figure 13:
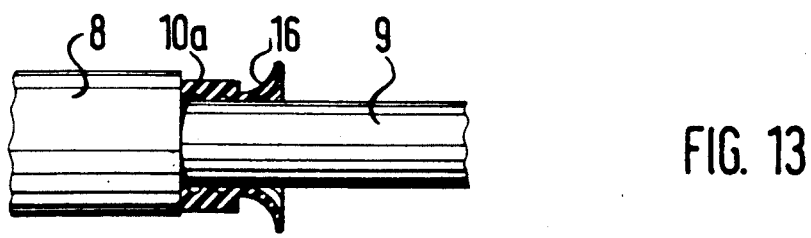

Alternatively, in FIG. 13, the sealing element 10a has the distal end also secured in the tube 8 and the proximal end formed as a sealing annular lip 16.

By contrast to FIGS. 9 to 13, the cylindrical sealing element 10 may be fastened to the inner surface 4a of the channel 4, so that the lips 12, 13, the pins 14 or the lips 15 and 16 are directed inwards radially and are placed in sealing contact at the distal end of the channel 4 against the outer periphery of the tube 8 securing the branches 7 of the cutting loop.

As shown in FIG. 7, the sealing element 10 may also be arranged at the proximal end of the channel 4.

The embodiments according to FIGS. 2 to 6 have the advantage that the cutting loops produced until now and available commercially may be used without modification.

Since cutting loops may be considered as disposable, the embodiment according to FIGS. 9 to 13 may be more advantageous, since the seal is then assured throughout the period of operation of the insert.

What is claimed is:

1. An operating insert for a resectoscope, having a longitudinal channel therethrough with proximal and distal ends, an elongate electrode stem extending from an electrode carrier into said channel at a proximal end thereof, a tube extending within said channel and a cutting loop projecting from the distal end of said channel, said cutting loop having a pair of branches which are secured in said tube and merge into said electrode steam at their proximal ends, wherein sealing means are provided within said channel, said sealing means having radially extending projections which bear against one of said tube, said stem or said channel and allowing axial movement of said stem and said tube within said channel but preventing the passage of fluid to the proximal end of said channel.

2. An operating insert as claimed in claim 1 wherein the sealing means comprises a cylindrical sealing element which is mounted on a proximal end of the tube, the sealing element having projections which bear against the inner surface of the channel.

3. An operating insert as claimed in claim 1, wherein the sealing means comprises a cylindrical sealing element which is mounted on the inner surface of the channel, the sealing element having projections which extend radially inwardly.

4. An operating insert as claimed in claim 3, wherein said cylindrical sealing element is positioned so that its projections bear against the outer surface of the tube.

5. An operating insert as claimed in claim 3, wherein said cylindrical sealing element is positioned so that its projections bear against the outer surface of the stem.

6. An operating insert as claimed in claim 2, wherein the sealing element is of plastics material and has an annular constriction on which the projections are provided, the projections comprising encircling sealing lips which are transversely slotted.

7. An operating insert as claimed in claim 2, wherein the sealing element is of plastics material and has an annular constriction on which the projections are provided, the projections comprising sealing lips which form partial rings, with mutually overlapping end regions.

8. An operating insert as claimed in claim 2, wherein the sealing element is of plastics material and has an annular constriction on which the projections are provided, the projections comprising closely spaced radially extending pins.

9. An operating insert as claimed in claim 3 wherein the sealing element is of plastics material and has an annular constriction on which the projections are provided, the projections comprising encircling sealing lips which are transversely slotted.

10. An operating insert as claimed in claim 3 wherein the sealing element is of plastics material and has an annular constriction on which the projections are provided, the projections comprising sealing lips which form partial rings, having mutually overlapping end regions.

11. An operating insert as claimed in claim 3 wherein the sealing element is of plastics material and has an annular constriction on which the projections are provided, the projections comprising closely spaced radially extending pins.

12. A resectoscope which comprises, in combination, a resectoscope shaft and an operating insert insertable within said shaft of said resectoscope, said insert comprising a longitudinal channel therethrough with proximal and distal ends, an elongate electrode stem extending from an electrode carrier into said channel at a proximal end thereof, a tube extending within said channel and a cutting loop projecting from the distal end of said channel, said cutting loop having a pair of branches which are secured in said tube and merge into said electrode stem at their proximal ends, wherein sealing means are provided within said channel, said sealing means having radially extending projections which bear against one of said tube, said stem or said channel and allowing axial movement of said stem and said tube within said channel but preventing the passage of fluid to the proximal end of said channel.

* * * * *